United States Patent
Bocquenet et al.

(10) Patent No.: US 6,835,830 B1
(45) Date of Patent: Dec. 28, 2004

(54) METHOD FOR EVAPORATING AMINONITRILE

(75) Inventors: Gerald Bocquenet, Communay (FR); Henri Chiarelli, Communay (FR); Philippe Leconte, Meyzieu (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/720,598

(22) PCT Filed: Jun. 24, 1999

(86) PCT No.: PCT/FR99/01524

§ 371 (c)(1),
(2), (4) Date: May 7, 2001

(87) PCT Pub. No.: WO99/67214

PCT Pub. Date: Dec. 29, 1999

(30) Foreign Application Priority Data

Jun. 25, 1998  (FR) ............................ 98 08258

(51) Int. Cl.$^7$ ......................................... C07D 201/108
(52) U.S. Cl. ..................................................... 540/539
(58) Field of Search ........................ 540/539; 558/361

(56) References Cited

U.S. PATENT DOCUMENTS 3,658,810 A  * 4/1972 Tanaka et al. ........... 260/239.3
6,262,259 B1 * 7/2001 Cotting et al. .............. 540/539

FOREIGN PATENT DOCUMENTS

WO         98/37063    * 8/1998

* cited by examiner

Primary Examiner—Rita Desai
Assistant Examiner—Robert Shiao
(74) Attorney, Agent, or Firm—Burns, Doane, Swecker & Mathis, L.L.P.

(57) ABSTRACT

The invention concerns a method for evaporating aminonitrile and water in conditions limiting or eliminating the formation of heavy by-products in particular aminocarboxylic acid oligomers. To avoid said inconvenience, said method for evaporating aminonitrile and water is characterised in that the water in vapour state serves as balance gas for evaporation.

11 Claims, No Drawings

METHOD FOR EVAPORATING AMINONITRILE

This appln is a 371 of PCT/FR99/01524 filed on Jun. 24, 1999.

The present invention relates to the vaporization of aminonitrile and water under conditions which limit or eliminate the formation of heavy by-products, especially aminocarboxylic acid oligomers.

The reaction between an aminonitrile and water results in the formation of lactam, especially caprolactam when 6-aminocapronitrile is employed.

This reaction can be carried out in liquid phase with heating and under elevated pressure. It can also be carried out in vapour phase. For this second embodiment, it is therefore necessary to convert the aminonitrile and the water to the vapour state. For examples of carrying out aminonitrile hydrolysis in vapour phase reference may be made, in particular, to the patent EP-A-0 659 741 and the international application WO-A-96/22974.

The choice of the manner of vaporization of the aminonitrile and water is not trivial.

In fact, it is possible to consider forming a liquid water/aminonitrile mixture and then heating this mixture to a temperature sufficient to vaporize the two components. In this case, the formation of heavy compounds having an amide function or carboxylic salt function (oligomers) is observed. These compounds are capable of attaching themselves, at least in part, to the catalyst and so reducing its service life. Furthermore, they deposit in the apparatus, and foul it. This necessitates periodic cleaning of the said apparatus and hence the relatively frequent shutdown of the plant, with all the economic consequences, as can be imagined.

Another technique which could be considered would be to vaporize the streams of aminonitrile and water separately. The Applicant has noted that, at the temperatures required to vaporize the aminonitrile, it undergoes decomposition, in considerable proportions, to give a compound of the amidine or polyamidine type (condensation of two or more molecules of aminonitrile with elimination of ammonia).

In order to avoid these various drawbacks, a process for vaporizing aminonitrile and water has now been found which is characterized in that the water, in the vapour state, is used as the carrier gas for this vaporization.

The decomposition of the aminonitrile depends on the evaporation temperature and on the residence time of the liquid during its evaporation. In the process of the invention, therefore, the residence time of the liquid is minimized by the technology of the evaporator and the water in the vapour state reduces the partial pressure of the aminonitrile, so lowering its evaporation temperature.

The molar ratio of water to aminonitrile can vary greatly in the process of the invention. It depends essentially on the cyclizing hydrolysis process in which the reactants will be deployed. This molar ratio between the water and aminonitrile employed is commonly between 0.5 and 106 and preferably between 1 and 20. The upper value of this ratio is not critical for the invention, although higher ratios are of virtually no interest for the hydrolysis reaction on economic grounds.

Generally, the water vapour will be at a temperature of from 120° to 600° C. and preferably from 200 to 550° C.

The aminonitrile will generally be employed at a temperature of from 20 to 300° C. Preferably, this temperature will be from 100 to 250° C.

The aminonitrile/water vapour mixture is brought rapidly in a heat exchanger to a temperature at which the vaporization of the mixture is complete.

If appropriate, this temperature can be that at which the reaction between the aminonitrile and water will be conducted. Such a reaction temperature is commonly between 200 and 450° C. and preferably between 250 and 400° C.

The absolute pressure at which the vaporization of the aminonitrile is conducted is generally from 0.1 to 3 bar.

The aminonitrile employed in the process of the invention is more particularly a linear or branched aliphatic aminonitrile having 3 to 12 carbon atoms.

By way of examples, mention may be made more particularly of the aliphatic aminonitriles originating from the hydrogenation to a primary amine function of one of the two nitrile functions of dinitriles such as adiponitrile, methylglutaronitrile, ethylsuccinonitrile, dimethylsuccinonitrile, malononitrile, succinonitrile, glutaronitrile and dodecanedinitrile.

The most important aminonitrile is 6-aminocapronitrile, the cyclizing hydrolysis of which leads to caprolactam, whose polymerization yields nylon 6.

For convenience, in the text below, reference may be made more particularly to 6-aminocapronitrile (or ACN).

The process is performed with the aid of a system without retention of liquid.

The technologies which can be employed in order to limit the residence time of the product in liquid phase during the evaporation are of two types:

evaporation of the aminonitrile as a film on a heated surface;

evaporation of an at least partly liquid mist of aminonitrile in the superheated water vapour; in this case, the instances of contact between liquid and hot wall are replaced by contact between gas and liquid droplets.

In the case of evaporation as a film on a heated surface, the heat required for the evaporation is supplied on the one hand by the appreciable heat of the vapour and of the aminonitrile and on the other hand by transfer of heat across the evaporating surface. The evaporator is of the falling-film evaporator type.

The liquid can be distributed over the tubes of the evaporator in accordance with the distribution systems generally employed in this type of technology:

supply of the at least partly liquid aminonitrile to the tube plate, then distribution of this aminonitrile in each tube;

distribution of the at least partly liquid aminonitrile in each tube by atomization to a mist of the aminonitrile above the tube plate; this technology has the advantage over the preceding one of reducing further the residence time in liquid phase at high temperature; the liquid can be atomized by means of a nozzle which is fed with the liquid alone or, better still, by a nozzle which is fed simultaneously with the liquid and the water vapour.

In the case of evaporation in a mist with contact between gas and water droplets, all of the heat is supplied by the appreciable heat of the two components, the aminonitrile, which is at least partly in liquid phase, and the water in vapour phase.

The temperature of the water vapour and the temperature of the at least partly liquid aminonitrile are selected such that the mist obtained is at a temperature which is either equal to or greater than the dew point of the water/aminonitrile mixture which makes up the said mist. Obviously, the dew point depends on the ratio of water to aminonitrile and is easily determined for the selected ratio.

Thus, by way of example, at atmospheric pressure, the dew point is 180° C. for a water/6-aminocapronitrile (ACN) ratio of 4, 110° C. for a water/ACN molar ratio of 56, 210° C. for a water/ACN ratio of 1, and 230° C. for pure ACN.

This evaporation in a mist by contact between gas and liquid droplets can be single-stage or multistage. If the evaporation is single-stage, the temperatures of the aminonitrile and of the water vapour are such that the vaporization of the liquid can be total or partial. If the evaporation is multistage, the stream of aminonitrile, preheated to 230° C., for example, is divided into a number of portions, three or four; the first portion of this liquid is mixed with the superheated water vapour, at 300° C. for example, such that all of the liquid is vaporized, the temperature of the mixture reducing simultaneously to around the dew point as a consequence of the vaporization. The mixture in the vapour state is subsequently superheated, to 300° C. for example, and then mixed again with the second portion of the liquid, which vaporizes in turn; the procedure is repeated for as many times as is necessary to obtain the total vaporization of the liquid. In this process, the mist of liquid is generated at each stage by means of atomizing nozzles, the mixture being subsequently made in a volume sufficient to ensure the total evaporation of the liquid.

The system for vaporizing the aminonitrile will preferably be selected such that the dwell time of liquid aminonitrile in the said system, comprising the preheating of the said aminonitrile, is less than or equal to one minute, preferably less than or equal to 5 seconds.

The examples which follow illustrate the present invention.

EXAMPLE 1

200 g/h of 6-aminocapronitrile (ACN), preheated to 230° C., and 129 g/h of water vapour at 300° C. are injected through a 1 mm nozzle.

The mist thus formed is vaporized, then superheated to 300° C. with the aid of an exchanger before it supplies a hydrolysis reactor containing 162 g of alumina, the said reactor being maintained at 300° C.

Over more than 400 h of operation, no reactor fouling nor any reduction in catalytic activity (measured by the rate of conversion of ACN at a constant flow rate equal to 99%) was observed.

COMPARATIVE TEST 1

329 g/h of an ACN/water mixture containing 61% by weight ACN are fed into a 200 ml evaporator heated at 300° C.

The gaseous mixture emerging from the evaporator is passed to a hydrolysis reactor containing 162 g of alumina, the said reactor being maintained at 300° C.

The test is stopped after 172 h of operation. During this period, the rate of conversion of ACN has passed from 99% to 95%.

Following disassembly of the apparatus, the presence of a solid (nylon 6) is noted inside the evaporator and at the entrance of the hydrolysis reactor (25% of the height of the contents of the said reactor have solidified).

What is claimed is:

1. Process for producing a lactam by a reaction between water vapor and a linear or branched aliphatic aminonitrile having 3 to 12 carbon atoms in vapor phase and in presence of a catalyst, comprising providing water in vapor phase to an evaporator, and vaporizing the aminonitrile by feeding the aminonitrile in liquid phase to the evaporator, wherein the aminonitrile in liquid phase is contacted with the water vapor in the evaporator, and subsequently introducing the resulting mixture of aminonitrile and water vapor into a hydrolysis reactor in which the resulting mixture is contacted with the catalyst, and wherein the aminonitrile originates from a hydrogenation to a primary amine function of one of the two nitrile functions of a dinitrile selected from the group consisting of adiponitrile, methylglutaronitrile, ethylsuccinonitrile, dimethylsuccinonitrile, malononitrile, succinonitrile, glutaronitrile and dodecanedinitrile.

2. Process according to claim 1, wherein the water vapor is fed at a temperature of from 120° to 600° C.

3. Process according to claim 1, wherein the aminonitrile is fed at a temperature of from 20° to 300° C.

4. Process according to claim 1, wherein the resulting mixture of aminonitrile in the water vapor that is obtained is brought to the temperature of reaction between the aminonitrile and water.

5. Process according to claim 1, wherein the aminonitrile is a linear or branched aliphatic aminonitrile having 3 to 12 carbon atoms.

6. Process according to claim 1, wherein the vaporization of the aminonitrile is conducted under an absolute pressure of from 1 to 3 bar.

7. Process according to claim 1, wherein the vaporization step is performed with a system without retention of liquid.

8. Process according to claim 1, wherein the vaporization of the aminonitrile is performed with a dwell time of liquid aminonitrile in the vaporization step being less than or equal to one minute.

9. Process for producing a lactam by a reaction between water vapor and a linear or branched aliphatic aminonitrile having 3 to 12 carbon atoms in vapor phase and in the presence of a catalyst, comprising providing water in vapor phase to an evaporator, and vaporizing the aminonitrile by feeding the aminonitrile in liquid phase to the evaporator, wherein the aminonitrile in liquid phase is contacted with the water vapor in the evaporator, and subsequently introducing the resulting mixture of aminonitrile and water vapor into a hydrolysis reactor in which the resulting mixture is contacted with the catalyst, and wherein the aminonitrile is fed as a film on a heated surface, in a falling-film evaporator.

10. Process for producing a lactam by a reaction between water vapor and a linear or branched aliphatic aminonitrile having 3 to 12 carbon atoms in vapor phase and in the presence of a catalyst, comprising providing water in vapor phase to an evaporator, and vaporizing the aminonitrile by feeding the aminonitrile in liquid phase to the evaporator, wherein the aminonitrile in liquid phase is contacted with the water vapor in the evaporator, and subsequently introducing the resulting mixture of aminonitrile and water vapor into a hydrolysis reactor in which the resulting mixture is contacted with the catalyst, and wherein the aminonitrile is atomized in the fed water vapor.

11. Process for producing a lactam by a reaction between water vapor and a linear or branched aliphatic aminonitrile having 3 to 12 carbon atoms in vapor phase and in the presence of a catalyst, comprising providing water in vapor phase to an evaporator, and vaporizing the aminonitrile by feeding the aminonitrile in liquid phase to the evaporator, wherein the aminonitrile in liquid phase is contacted with the water vapor in the evaporator, and subsequently introducing the resulting mixture of aminonitrile and water vapor into a hydrolysis reactor in which the resulting mixture is contacted with the catalyst, wherein liquid aminonitrile is fed into water vapor to produce a mixture of water vapor and aminonitrile and the resulting mixture brought rapidly in a heat exchanger to a temperature at which vaporization of the mixture is complete.

* * * * *